United States Patent [19]

Nazar

[11] Patent Number: 5,678,424
[45] Date of Patent: Oct. 21, 1997

[54] RECTIFIED REFLUX DEETHANIZER

[75] Inventor: Behzad Nazar, Los Angeles, Calif.

[73] Assignee: Brown & Root, Inc., Alhambra, Calif.

[21] Appl. No.: 589,167

[22] Filed: Jan. 22, 1996

Related U.S. Application Data

[60] Provisional application No. 60/005,825, Oct. 24, 1995.
[51] Int. Cl.⁶ ............................................. F25J 1/00
[52] U.S. Cl. ................................. 62/630; 62/935
[58] Field of Search .............................. 62/630, 935

[56] References Cited

U.S. PATENT DOCUMENTS

| | | |
|---|---|---|
| 1,735,558 | 11/1929 | Youker . |
| 1,954,839 | 4/1934 | Youker . |
| 1,957,818 | 5/1934 | Carney . |
| 2,327,134 | 8/1943 | Schuftan ........................ 62/935 |
| 2,327,643 | 8/1943 | Houghland . |
| 3,956,415 | 5/1976 | Cummings et al. ............ 62/935 |
| 4,285,708 | 8/1981 | Politte et al. . |
| 4,430,102 | 2/1984 | Tedder ........................... 62/935 |
| 4,436,540 | 3/1984 | Dowd et al. . |
| 4,720,293 | 1/1988 | Rowles et al. . |
| 4,726,826 | 2/1988 | Crawford et al. . |
| 4,900,347 | 2/1990 | McCue, Jr. et al. . |
| 5,035,732 | 7/1991 | McCue, Jr. . |
| 5,235,479 | 8/1993 | DiCintio et al. . |

OTHER PUBLICATIONS

"Ethylene from NGL Feedstocks–Part 3", K. Ng et al, Hydrocarbon Processing, Dec. 1983, pp. 99–103.
"Ethylene From NGL Feedstocks–Part 4", H. Kister et al Hydrocarbon Processing, Jan. 1984.
"Temperature–Heat Diagrams For Complex cols. 2. Underwood's Method For Side Strippers and Enrichers", N.A. Carlberg, Ind. Eng. Res, vol. 28, pp. 1379–1386, 1989.

*Primary Examiner*—Ronald C. Capossela
*Attorney, Agent, or Firm*—Lyon & Lyon LLP

[57] ABSTRACT

The present invention is an improvement in the combined fractionation steps of deethanization and C2 splitting for ethylene and ethane separation. Theoretical stages are added to the rectification section of a deethanizer above a liquid or vapor sidedraw. Polymer grade ethylene product up comprising to 30 percent of the ethylene in the deethanizer feed is obtained in an overhead stream according to the present invention. Lesser recovery at the same ethylene purity or higher recovery at lower ethylene purity are obtained varying recovery or numbers of additional stages in the rectification. An overall reduction in total cold utilities for the overhead condensers for the deethanizer and downstream C2 splitter are obtained in practicing the present invention.

12 Claims, 5 Drawing Sheets

RECTIFIED REFLUX DEETHANIZER

This is a continuation-in-part of provisional patent application Ser. No. 60/005,825 filed Oct. 24, 1995.

The present invention relates to the fractionation of light hydrocarbons. The present invention especially relates to deethanization.

BACKGROUND

The present invention relates to deethanization and ethylene/ethane splitting fractionation steps of cracked gases for olefin recovery. In order to properly appreciate the technological field of the fractionation trains used for separation of olefins from other components in cracked gas, the article "Ethylene from NGL feedstocks—Part 3 Flow Scheme Comparison" (K. Ng et al, Hydrocarbon Processing, Dec. 1983, pp. 99–103) is referred to herein to describe the three most typical choices for the first fractionation step in the fractionation train. A front-end demethanizer, deethanizer and depropanizer are evaluated for their advantages in fractionating cracked gas from NGL feeds. The front-end deethanizer was found, under the assumptions made at the time of the article, to be the most preferable of the fractionation trains.

The article "Ethylene from NGL feedstocks—Part 4 Low Pressure C2 Splitter" (H. Z. Kister et al, Hydrocarbon Processing, Jan. 1984) describes an optimized fractionation step required in olefins separation of cracked gas. The low pressure ethylene/ethane splitter ("C2 splitter") is preferred for the potential for heat pumping the column and therein provide an open ethylene refrigeration loop for other refrigeration needs in the fractionation train. The C2 splitter has been the focus of much study to reduce the relatively expensive utilities required for separation of ethylene and ethane, which have relatively close boiling components.

Other concepts in the prior art that relate to the present invention are described below.

U.S. Pat. No. 1,735,558 describes a multiple sidedraw column crude oil fractionation column. The vapor from three sidedraws from a first column is partly condensed and is condensed and rectified in a second column. The liquid of the second column is returned to the first column for stripping.

U.S. Pat. No. 1,954,839 describes a distillate rectification in which a the feed is partly vaporized and the vapor and liquid phases separated three times to provide for multi-level feeds to a fractionation column. The liquid separated from the last of partial fractionation stages is recovered as the distillate product.

U.S. Pat. No. 1,957,818 describes rectification of light hydrocarbons and mentions ethylene and ethane as among those. In a series of refluxed and stripped columns, the patent describes using a condensed, rectified overhead stream as feed to a next column. A stripped bottoms stream of the next column is fed to the rectification section of the first column.

U.S. Pat. No. 2,327,643 describes a two column, dual pressure fractionation method wherein the column pressures are chosen to accommodate vaporization of the condensed overhead stream of a second column acting to indirectly supply part of the condensing duty for the overhead stream of a first column. The vaporized second column vapor is recompressed and is fed to the bottom of the first column to supply reboiling duty for the first column.

U.S. Pat. No. 4,285,708 describes a two column method for a single deethanization using a split feed concept. The gaseous feed stream to the deethanization is split and a portion is condensed and stripped in a stripping column. The overhead vapor from the stripping column is partially condensed and fed to the rectification section of the deethanizer column. The stripping duty of the deethanizer column and the rectification section diameter are substantially reduced by use of an upstream stripping column.

U.S. Pat. No. 4,436,540 describes a full fractionation train for olefin recovery from cracked gas using only low pressure rectification columns for gaseous portions of the pyrolysis furnace effluent. Liquid portions of the rectification columns are further fractionated in high pressure refluxed and stripped columns to complete the separation. Partial inter-condensation by pumparounds and liquid streams from the high pressure columns provide rectification duty to the rectification columns.

U.S. Pat. No. 4,720,293 describes a method of feed conditioning to a demethanizer for an olefins fractionation train. The fractionation train's first separation column is the demethanizer, and the feed to it is treated in a dephlegmator to recover ethylene. Column 100 describes a pasteurizing section accommodating removal of residual hydrogen from an overhead ethylene product.

U.S. Pat. No. 4,900,347 describes a system of multiple dephlegmations integrated into a demethanization of an olefins recovery stream. The multiple rectifications in three dephlegmators produce three liquid bottoms streams that are fed to two refluxed demethanization columns. A dephlegmated portion of the feed gas is fed to a second demethanizer column. The overhead product of a first demethanizer is also fed to the second demethanizer. The bottom product of the second demethanizer is a relatively pure stream of ethylene.

U.S. Pat. No. 5,035,732 describes a system similar to that of U.S. Pat. No. 4,900,347, although the second demethanizer is operated at low pressure.

U.S. Pat. No. 5,253,479 describes forming a product specification liquid stream of ethylene as a bottom product of a demethanator column, wherein a portion of the ethylene stream is used as an absorbing, lean liquid in an absorber column. The gas feed to the bottom of the absorber column is the gaseous portion of a partially condensed cracked gas stream comprising at least hydrogen, methane, ethylene and ethane. The absorbing-liquid ethylene and its captured components are fed to a deethylenization column, from which the overhead vapor stream is fed entirely to the demethanator column. It is an apparent disadvantage of the patent process wherein the ethylene condensed at considerable cost in utility must be vaporized in the deethylenizer and re-condensed in the demethanator.

In the article "Temperature-Heat Diagrams for Complex Columns, 2. Underwood's Method for Side Strippers and Enrichers" (N. A. Carlberg et al, Ind. Eng. Chem. Res., vol. 28, pp. 1379–1386, 1989), complex columns are described as having benefits and disadvantages. On page 1385, the authors state, "The question to ask is how do complex columns compare against simple column sequences in terms of utility consumption. The answer is that complex columns are more energy efficient but have larger temperature ranges than simple column sequences. Basically, complex columns are more favorable with respect to first-law effects and less favorable with respect to second-law effects. Thus, if there is an adequate temperature driving force, complex columns will be favored; if not, simple columns are more favorable from a utility point of view." A method is presented in the article for evaluating minimum reflux for complex column, i.e. those with one or more side strippers or enrichers. In the article, the operational definition of a side stripper or enricher is a device that withdraws from a column a sidestream vapor or liquid and returns to the same stage a stream comprising liquid or vapor generated in a second column. Side stripping or enriching necessarily returns to the fractionation column a portion of the withdrawn stream which has been enriched or stripped of its original components.

It will be apparent from the above that a simplified and relatively inexpensive method for reducing the combined condensation duties of a demethanizer—deethanizer—C2 splitter combination has not been previously developed. It is an object of the present invention to make such an improvement.

SUMMARY OF THE INVENTION

The present invention is directed to at least a portion of fractionation train wherein ethylene is separated from cracked gas or from a combination with light hydrocarbons from other sources, such as from the gaseous products of fluid catalytic cracking of hydrocarbons. More specifically, the present invention is directed to processing a demethanized stream of cracked gas in a deethanizer, wherein a deethanizer overhead product stream is obtained comprising an ethylene purity of at least product specification, although a lesser degree of ethylene purity may be obtained in that overhead stream depending on the desired processing requirements. It is a requirement of the present invention to add theoretical stages to the rectification section of a prior art deethanizer wherein stages were originally designed to effect only a minimum separation of ethane and ethylene from heavier components. Conceptually, the present invention is applicable to a combination of a deethanizer and an ethylene/ethane fractionation column, where an overhead product stream is "split" or fractionated downstream of a first column to obtain the desired product. The art of fractionation train design has developed in a similar sense for obtaining propylene and propane from heavier components, as well as for butylene and butane from a stream with heavier products. The present invention is thus applicable in concept to separations made wherein (1) an overhead product stream comprising at least two product components is separated as an overhead product in a first column and (2) at least two product components of the overhead product stream are separated in a second column to form two product streams.

It has been found, quite surprisingly, (1) that a deethanizer separating ethylene and ethane from heavier components produces an overhead product stream such that ethylene purity and/or recovery may be varied over a broad range for that stream and (2) that the cold utilities of the deethanizer overhead condenser are substantially the same regardless of the ethylene purity or degree of recovery of ethylene in the overhead product stream. To accomplish this surprising result, a sidedraw must be withdrawn from the rectification section of the deethanizer comprising a significant part of the column feed components in the rectification section. No portion of the sidedraw stream is returned to the deethanizer, although processes with such partial return of sidedraw streams are well established and defined in the prior art. Such partial or total return of sidedraw streams are shown and described for side enrichers in the Carlberg et al article above or are well known in the art of partial or total intercondensing for rectification sections. Although for the specific example below, it is preferable to withdraw with the sidedraw of the present invention substantially all the ethane in the deethanizer feed and about 70 percent of the ethylene to obtain a polymer grade ethylene product from the deethanizer overhead product stream, such a description is not a limitation of the present invention regarding recovery of polymer grade ethylene from the overhead product stream of a deethanizer. Subsequent fractionation in the C2 splitter of a sidedraw stream from the deethanizer of the present invention requires a column of smaller diameter and significantly less condensing duty in the overhead condenser. Thus, the overall condensation duty for the overhead condensers for the deethanizer and C2 splitter is also significantly reduced.

The rectification stages added to the deethanizer to accomplish the objects of the present invention will control the purity of the ethylene in the overhead product of the deethanizer. It will be shown below graphically that any desired purity of ethylene (99.9 mole percent or less) may be obtained in the overhead product stream of the deethanizer, while varying the number of stages in the deethanizer or the amount of ethylene recovered in the overhead product to achieve optimum cost savings depending on equipment and utilities costs. Although a specific example of the present invention is presented in the description below, other very advantageous modes of the present invention will become apparent to the skilled person with that description when cost savings are optimized from comparison of costs of equipment and utilities in certain circumstances.

The sidedraw is subjected to additional fractionation, preferably in a low pressure, heat-pumped C2 splitter to separate the ethylene from the ethane in the sidedraw stream, although any prior art ethylene/ethane fractionation system is advantageously improved through lower capital and cold utilities costs with incorporation of the present invention. It is further preferable to process cracked gases derived from feeds such as propane, butane or naphthas. When the withdrawal rate of ethylene in the sidedraw is as high as 70 mole percent of the ethylene in the column feed, it has been found that about 43 actual trays or about 30 theoretical stages should be added to the rectification section above the withdrawal stage of the sidedraw to generate from the column overhead a stream of polymer grade ethylene, about 99.9 mole percent ethylene. The stages between the withdrawal stage for the sidedraw of the present invention in the deethanizer rectification section and the deethanizer overhead condenser shall hereafter be referred to as the "additional rectification section" of the deethanizer.

As described above, the additional rectification section preferably produces an overhead stream comprising polymer grade (or lesser quality as required) ethylene product equal to or less than about one third of the ethylene in the feed to the deethanizer, although any portion of said feed ethylene may be recovered thereby. The deethanizer reflux condenser duty in the present invention is relatively constant over the range of operation described below. For a specific example described below, an overhead product stream may be obtained containing less than about 60 percent of the ethylene in the deethanizer feed at a purity of about 98 mole percent ethylene. For the purpose of fractionation analysis herein, the efficiency of rectification section trays described herein is about 70 percent, such that reference to stages will mean theoretical stages and reference to trays will mean actual sieve trays.

It will be clear to the skilled person with disclosure of the present invention that the total refrigeration utilities for deethanization with an additional rectification section in combination with an ethylene/ethane fractionation (C2 splitting) are reduced over prior art combinations of deethanization and C2 splitting. Combined condenser duties for deethanization and C2 splitting can be reduced by up to about 24 percent for the preferred embodiment described below wherein polymer grade ethylene is produced as an overhead stream from the deethanizer. Greater savings in equipment cost and cold utilities will be obtained depending on further optimization of the present invention.

In summary, the method of withdrawing a sidedraw from a deethanizer without return of any portion of the sidedraw stream to the deethanizer creates, for components in the sidedraw stream, a refluxing stream comprising the liquid stream from the stage above the withdrawal stage. The refluxing is accomplished by rectifying the vapor stream leaving the withdrawal stage and returning it to the withdrawal stage having removed some substantial portion of the ethylene from the vapor leaving the withdrawal stage. Thus, the method of the present invention is also hereafter referred to as a "rectified reflux deethanizer". The "rectified reflux" of the present invention is that reflux needed to achieve a desired ethylene purity in the deethanizer overhead product (the separation of ethylene and ethane) as well as to obtain the desired ethylene/ethane recovery desired from the deethanizer feed (the separation of ethylene/ethane from propylene and heavier components. It will be appreciated that this combined refluxing, the rectified refluxing, achieves a surprising result with no further increase in cold utilities in the overhead condenser in the deethanizer over the prior art operation wherein no relatively pure ethylene stream is obtained.

In a further embodiment of the present invention, a prior art, existing deethanizer is converted ("revamped" or "retrofitted") to a rectified reflux deethanizer according to the present invention. The conversion or initial design of a deethanizer according to the present invention includes adding rectification section stages (the additional rectification section) to a column or providing a separate column in which the rectified reflux method is performed to obtain a high purity ethylene product or an ethylene product of lesser purity as desired.

DETAILED DESCRIPTION OF THE INVENTION

For the section of the deethanizer from the feed stage to a sidedraw withdrawal stage, the present invention operates similarly to a prior art deethanizer, wherein a sidedraw stream is withdrawn and further fractionated in a C2 splitter to recover ethylene from ethane and a reflux stream is provided to the sidedraw withdrawal stage from the stage above it. The present invention creates above the sidedraw withdrawal stage an additional rectification section at substantially the same pressure as the rest of the deethanizer wherein rectification of ethylene from ethane occurs without significant increase in cold utilities in the overhead condenser compared to a deethanizer without the additional rectification section. A comparison of a prior art deethanizer with a low pressure, heat-pumped C2 splitter is compared below with a deethanizer according to the present invention with a low pressure, heat-pumped C2 splitter.

PRIOR ART DEETHANIZER

Figure 1:
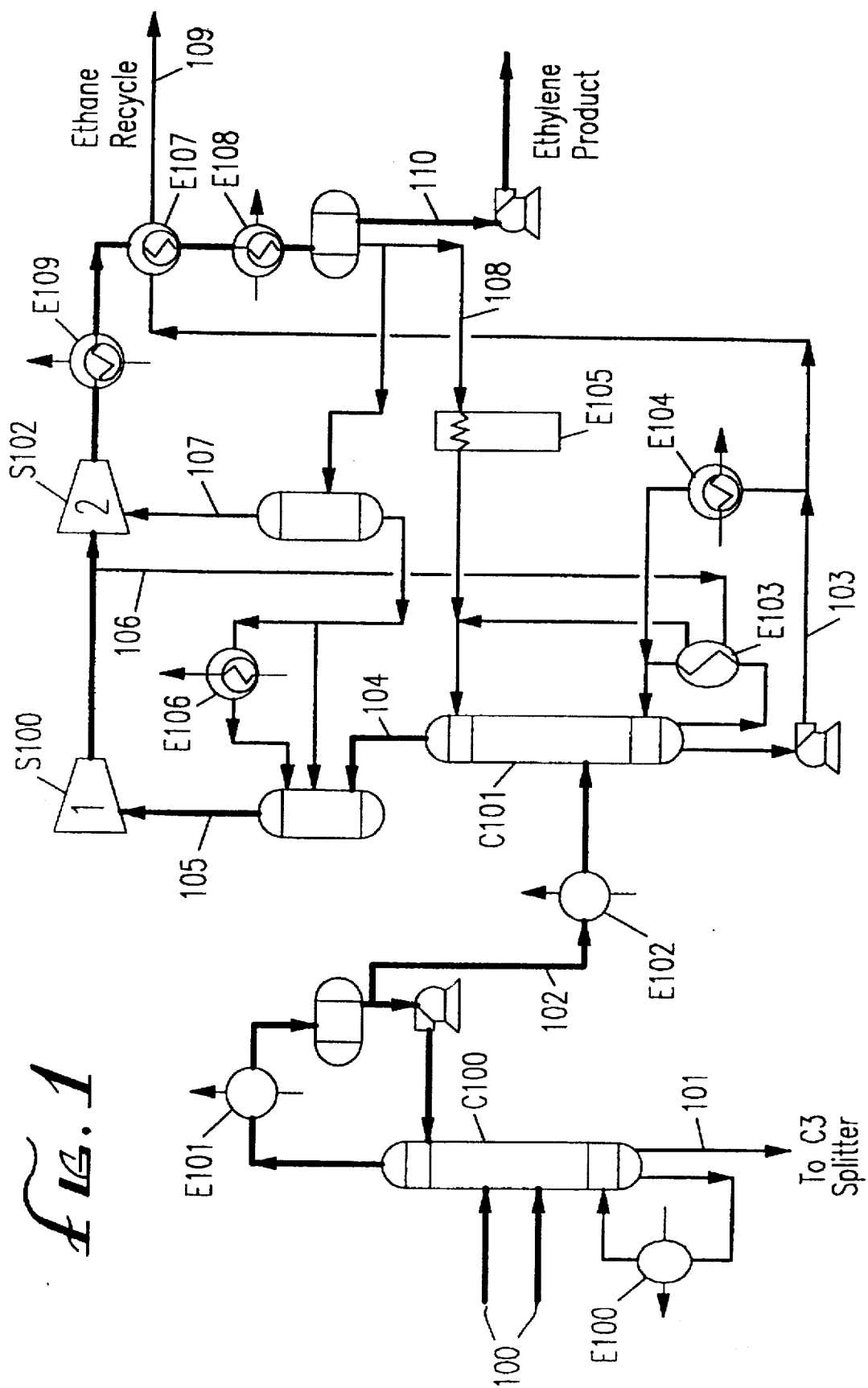
FIG. 1 is a prior art deethanizer combined with a heat pumped C2 splitter.

FIG. 1 is the prior art process comprising columns C100 (a deethanizer with a rectification and stripping section) and C101 (a low pressure, heat pumped C2 splitter). Other equipment noted in FIG. 1 are exchangers E100 (deethanizer reboiler, preferably heated with quench water), E101 (deethanizer overhead condenser, preferably cooled with propylene refrigerant), E102 (deethanizer overhead product partial vaporizer, preferably recovered to demethanizer feed chilling), E103 (C2 splitter heat pump reboiler), E104 (C2 splitter heat recovery reboiler, preferably chilling demethanizer feed), E105 (coldbox exchanger, preferably recovering process stream chilling), E106 (ethylene refrigeration load, preferably demethanizer feed chilling), E107 (ethane recycle vaporizer), E108 (ethylene refrigerant condenser, propylene refrigerant) and E109 (ethylene refrigerant cooler, propylene refrigerant), and stages S100/S101 (open ethylene refrigerant loop compressor stages, wherein S101 represents two compression stages). Stage S102 (not shown in FIG. 1) is described herein for the purpose of describing a comparative savings in compressor horsepower in the propylene refrigerant compressor, which supplies chilling in exchangers E108 and E109 to the ethylene refrigeration loop.

The process streams of FIG. 1 are streams 100 (upper and lower, i.e. vapor and liquid, streams of demethanized cracked gas), 101 (deethanizer bottoms stream), 102 (deethanizer overhead product), 103 (C2 splitter bottoms product), 104 (top stage vapor stream from the C2 splitter), 105 (lowest pressure stage drum vapor from the open ethylene refrigeration loop), 106 (heat-pumped C2 splitter reflux condensed in C2 splitter reboiler), 107 (highest pressure stage drum vapor from the open ethylene refrigeration loop), 108 (subcooled ethylene refrigerant loop condensate for C2 splitter reflux), 109 (ethane recycle, i.e. net bottoms product of the C2 splitter) and 110 (net ethylene product from the C2 splitter). Table 1 indicates the stream compositions, rates and conditions for this example.

The upper, vapor and lower, liquid streams, streams 100, from the demethanizer feed a feed stage section in column C100, defined by the upper and lower stages to which they are fed. Herein, the feed section will be referred to as a feed stage. Column C100 comprises 28 actual trays wherein streams 100 enter on trays 11 and 12 (the top tray of column C100 is tray 1). For purposes of column analysis for the detailed examples herein, tray efficiency in the rectification sections about 70 percent and in the stripping sections the tray efficiency is about 60 percent.

The condenser exchanger E101 and reboiler exchanger E100 provide cold, refluxing and hot, reboiling utilities to column C100 respectively. The relative amounts of C3's in the overhead product stream, stream 102, and the relative amounts of C2's in the bottom product stream, stream 101, indicate a commercially desirable level of separation of those components. This degree of separation will generally be repeated for the example with the present invention for purposes of comparison and is not a specific limitation of the present invention. The relative amounts of light hydrocarbons as stream components can vary widely depending on the source of the feed generating cracked gas.

The duty of exchanger E101 is about 50.9 MMBtu/hr for column C100 operating at about 240 psia. Stream 101, as indicated on FIG. 1, is preferably further fractionated in a C3 splitter (not shown).

Stream 102 is partially vaporized in exchanger E102 and fed to column C101 operating at about 60 psia, whose overhead stream, stream 104, enters the open refrigeration loop low pressure drum, combines with vaporized ethylene refrigerant to form stream 105, and wherein stream 105 feeds the first stage of the open refrigerant loop, stage S100. The compressed vapor from stage S100 is split, and one portion flows to the second stage of the compressor, stage 101, and the rest, stream 106, is condensed in the C2 splitter reboiler, exchanger E103, and the condensed stream is fed to the top stage of the C2 splitter as reflux. The compressed vapor from stage S102 is condensed in exchangers E107, E108 and E109. A portion of the condensed vapor from stage S102 is withdrawn as a net ethylene product, stream 110, while another portion is subcooled in exchanger E105 for use as column C101 reflux and the last portion of the stream is used as ethylene refrigerant, ultimately flowing to exchanger E106.

The net bottoms product of column C101, stream 109, is relatively pure ethane. Stream 103 contains stream 109, wherein a portion of stream 103 is used for demethanizer feed chilling. The refrigeration resulting from vaporizing the net ethane bottoms product of the C2 splitter is recovered to the ethylene refrigeration loop in exchanger E107. The conceptual operation of this low pressure, heat-pumped C2 splitter is substantially the same for this example and the next describing the present invention. Thus, the operation of the C2 splitter and the open ethylene refrigeration loop will not be discussed for the example of the present invention other than to point out significant differences between the prior art operation and that of the present invention shown in FIG. 2.

PRESENT INVENTION DEETHANIZER

Figure 2:
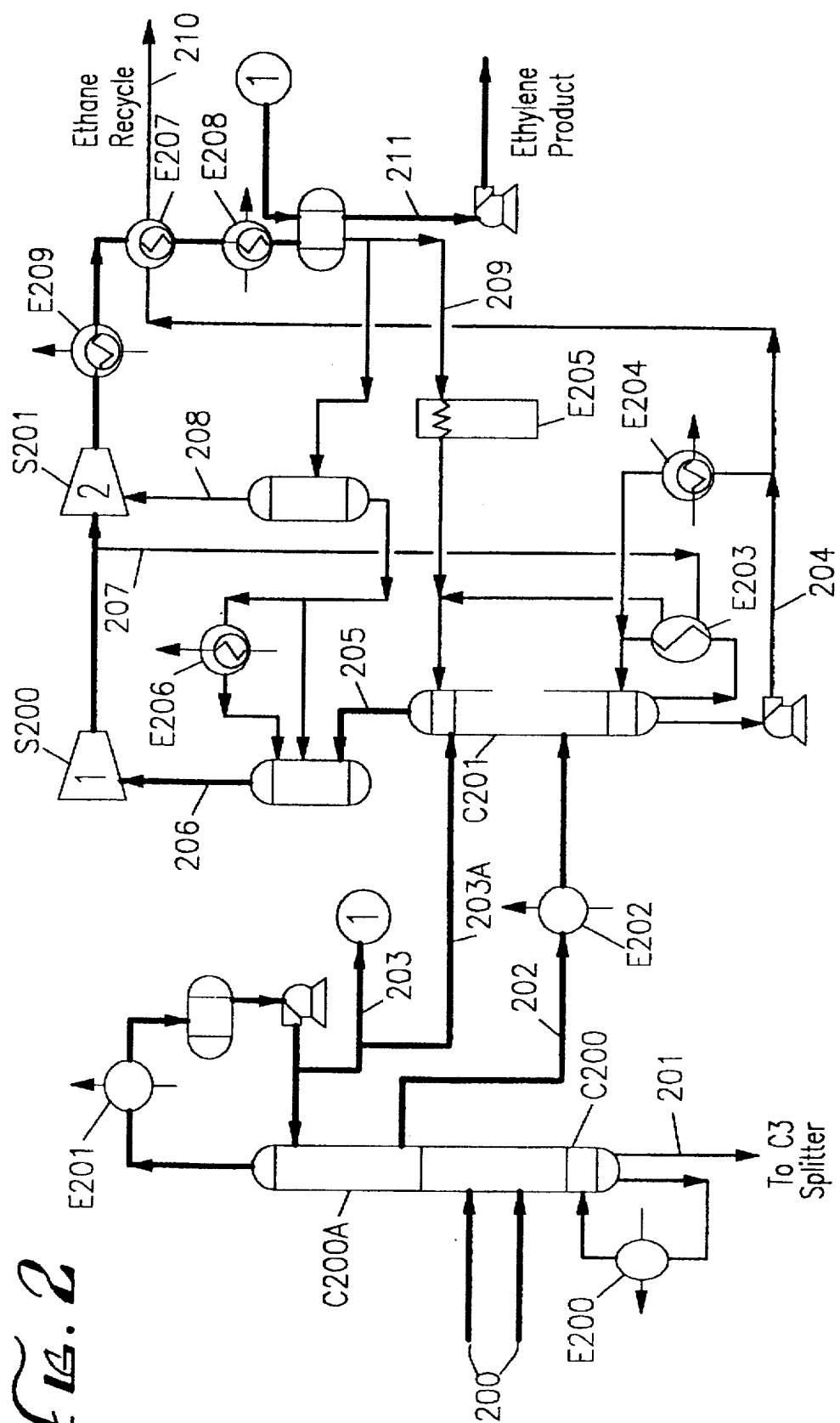
FIG. 2 is the present invention showing the additional rectification section added to the deethanizer of FIG. 1 combined with the heat pumped C2 splitter shown in FIG. 1.

FIG. 2 is the present invention comprising columns C200 (a deethanizer with a stripping section and a rectification section, wherein the rectification section comprises stages between a feed section and a sidedraw withdrawal stage and an additional rectification section, C200A, comprising stages between the sidedraw withdrawal stage and an overhead condenser) and C201 (a low pressure, heat pumped C2 splitter). Other equipment noted in FIG. 2 are exchangers E200 (deethanizer reboiler, preferably heated with quench water), E201 (deethanizer overhead condenser, preferably cooled with propylene refrigerant), E202 (deethanizer sidedraw stream partial vaporize, preferably recovered to demethanizer feed chilling), E203 (C2 splitter heat pump reboiler), E204 (C2 splitter heat recovery reboiler, preferably chilling demethanizer feed), E205 (coldbox exchanger, preferably recovering process stream chilling), E206 (ethylene refrigeration load, preferably demethanizer feed chilling), E207 (ethane recycle vaporizer), E208 (ethylene refrigerant condenser) and E209 (ethylene refrigerant cooler), and stages S200 and S201 (open ethylene refrigerant loop compressor stages, wherein S201 represents two compression stages). Stage S202 (not shown in FIG. 2) is described herein for the purpose of describing a comparative savings in compressor horsepower in the propylene refrigerant compressor, which supplies chilling in exchangers E208 and E209 to the ethylene refrigeration loop.

The process streams of FIG. 2 are streams 200 (upper and lower, i.e. vapor and liquid, streams of demethanized cracked gas), 201 (deethanizer bottoms stream), 202 (sidedraw stream), 203 (deethanizer overhead ethylene product stream), 203A (relatively impure deethanizer overhead ethylene product stream fed to the C2 splitter), 204 (C2 splitter bottoms product), 205 (top stage vapor stream from the C2 splitter), 206 (lowest pressure stage drum vapor from the open ethylene refrigeration loop), 207 (heat-pumped C2 splitter reflux condensed in C2 splitter reboiler), 208 (highest pressure stage drum vapor from the open ethylene refrigeration loop), 209 (subcooled ethylene refrigerant loop condensate for C2 splitter reflux), 210 (ethane recycle, i.e. net bottoms product of the C2 splitter) and 211 (net ethylene product from the C2 splitter). Table 2 indicates the stream compositions, rates and conditions for this example.

Table 3 is a comparative listing of the duties of the important heat exchangers for the processes shown in FIGS. 1 and 2. Table 4 is a comparative listing of the horsepower of the compression stages described for the embodiments of the prior art example shown in FIG. 1 and the present invention shown in FIG. 2. The horsepower for the propylene refrigeration compressor is shown as stage S102 for the process of FIG. 1 and as stage S202 for the process of FIG. 2. Stage S102 horsepower is represented as the word "BASE", as the total horsepower for the propylene compressor comprises many refrigeration loads other than those for C2 splitting. Stage S202 horsepower is represented as the word "BASE-996", indicating a savings of 996 horsepower over the BASE amount for the prior art embodiment of FIG. 1.

The deethanizer, column C200, comprises an additional rectification section, column C200A, wherein the vapor from the sidedraw withdrawal stage enters from the bottom and is rectified to form stream 203 or 203A. Column C200, operating at about 240 psia, comprises about 57 actual trays, wherein feed streams 100 enter on trays 41 and 42 (the top tray of column C200 is the number 1 tray). The sidedraw withdrawal stage is at tray number 30. Stream 203 is the sidedraw stream in FIG. 2 and is directed to a number "1", indicating its continuance on the other side of the figure at the other number "1" and inclusion of the overhead product stream of the deethanizer in the ethylene product drum. The duty required in the deethanizer overhead condenser, exchanger E201, for the degree of separation between streams 201, 202 and 203, as shown in Table 2 for all streams in this example, is about 50.7 MMBtu/hr.

The inclusion of stream 203A in FIG. 2 indicates a mode of operation wherein product specification ethylene in the overhead product stream of column C200 is not desired or cannot be achieved with the deethanizer. All or part of the overhead product stream is then directed as stream 203A to a stage higher in column C201 than stream 202, and the remaining portion of the overhead product stream, stream 203, if any, is directed to the ethylene product drum and recovered as stream 211, as indicated in FIG. 2. Alternatively, stream 203 may simply be used as a lower grade ethylene product than that obtained from the operation of the C2 splitting. For the present example, stream 203 achieves the a very high ethylene purity at the cost of about 29 additional actual trays to the deethanizer, column C200. In another embodiment of the present invention, significant equipment cost savings will be made wherein the function of exchanger E201 and its associated drum are incorporated into exchanger E208 and its associated product drum. For such an embodiment, the vapor stream from the top stage of column C200A is mixed with the process stream of the C2 splitter between exchangers E207 and E208, thereby eliminating an exchanger and a drum. Deethanizer reflux is obtained by pumping liquid ethylene from the drum associated with E208 to the top stage of column C200A.

The operation of column C200 and the associated heat-pumped, open refrigeration loop has been substantially described above. When the overall condensing duties of the deethanizer and the C2 splitter are compared for the processes shown in FIGS. 1 and 2, the savings in cold utilities equals about 24 percent for the present invention over the prior art design. Table 3 permits comparison of the duties for those duties. This utilities reduction is a benefit in addition to a substantial reduction in vapor and liquid traffic in the rectification section of the C2 splitter, indicating that reduction in column diameter would be recommended. The associated reduction in condensing duty in the C2 splitter indicates that a simple overhead condenser or the associated equipment for the open refrigeration loop also be reduced in size and cost.

In addition, it is known by the present invention that the purity of stream 203 or 203A can be such that it's purity is about the same specification obtained in the overhead product of the downstream fractionator. Alternatively, the purity of stream 203 or 203A can be obtained at any other desired purity and can be recovered either as product or sent to a downstream fractionation column for further fractionation. If a liquid product is obtained from the overhead stream of the deethanizer, column C200, the balance of condensed liquid from the overhead condenser is sent back as reflux to section C200A. It has been found that the liquid flow rate of "reflux" to the sidedraw withdrawal stage in column C200 from the stage above it is approximately equal to the liquid flow rate of the reflux to the top stage of column C100 in FIG. 1.

Figure 3:
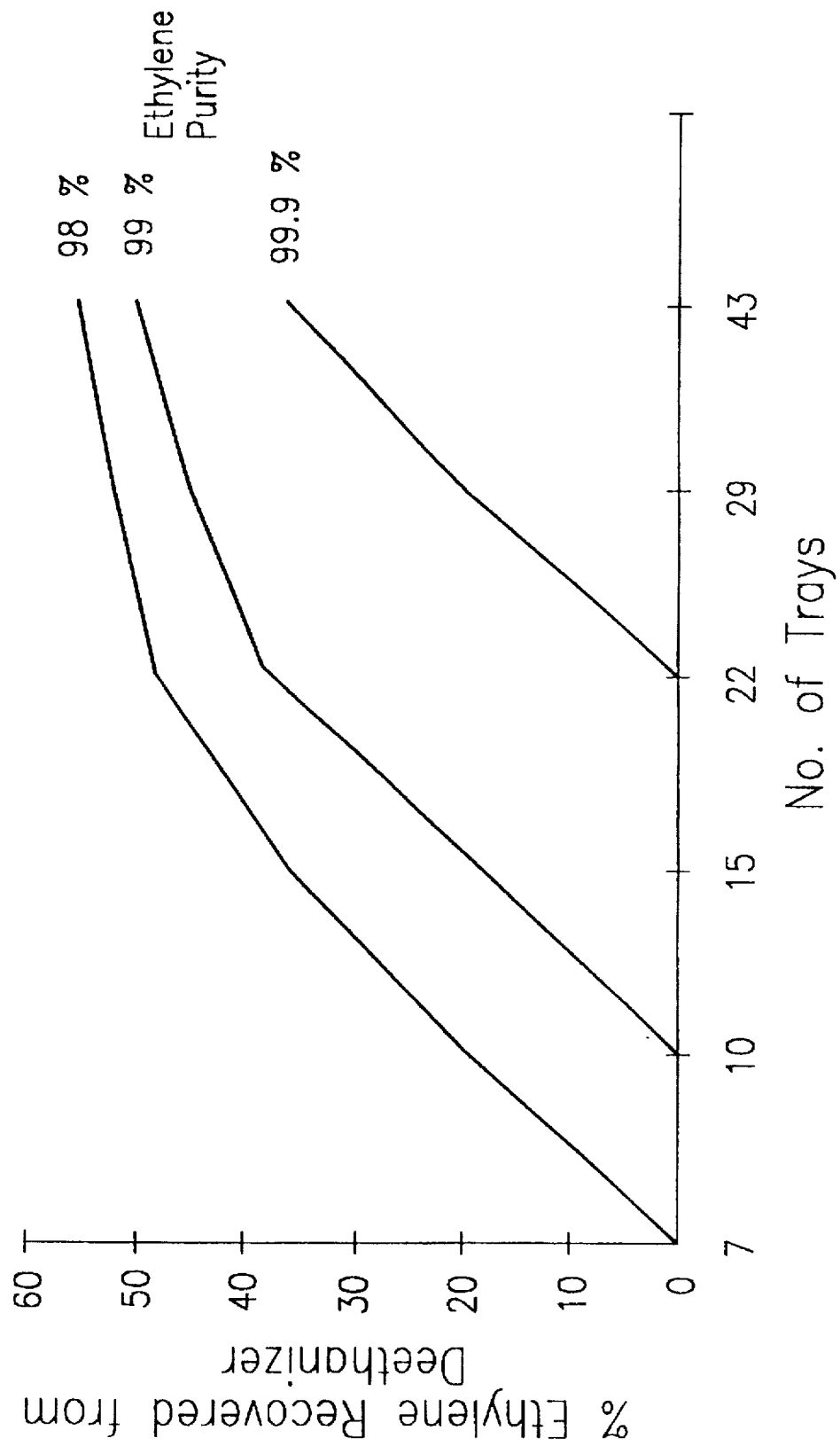
FIG. 3 is a graph of deethanizer-recovered ethylene compared with the number of actual trays required for three levels of ethylene purity desired in the overhead product of the rectified reflux deethanizer of the present invention.

FIG. 3 is a graphical representation of the extent of range of effective operation of the present invention for the type of feed described in Table 2 for the upper and lower streams 100. As an explanation of the features of FIG. 3, the actual trays in the additional rectification section, section C200A, are shown as the axis labeled "No. of Trays". The axis labeled "% Ethylene Recovered from Deethanizer" describes the percentage of the ethylene in upper and lower streams 200 in FIG. 2 and recovered in stream 203 of FIG. 2. The lines labeled "98%", "99%" and "99.95%" indicate the purity of the ethylene obtained in stream 203 by operation of section C200A according to the present invention from fractionation of a cracked gas stream derived from propane. It will be apparent to the skilled person that a further extension of the plot shown in FIG. 3 will permit accurate evaluation of the stages necessary for higher recovery of ethylene to the overhead product stream of the deethanizer.

The present invention may be advantageously used with C2 Splitters of any configuration. The rectification of a vapor from the sidedraw withdrawal stage in an additional rectification section is critical to the practice of the present invention. As demonstrated by the comprehensive results shown in FIG. 3, the present invention has wide ranging application for fractionation of cracked gases with substantial savings in equipment and refrigeration utilities costs.

Figure 4:
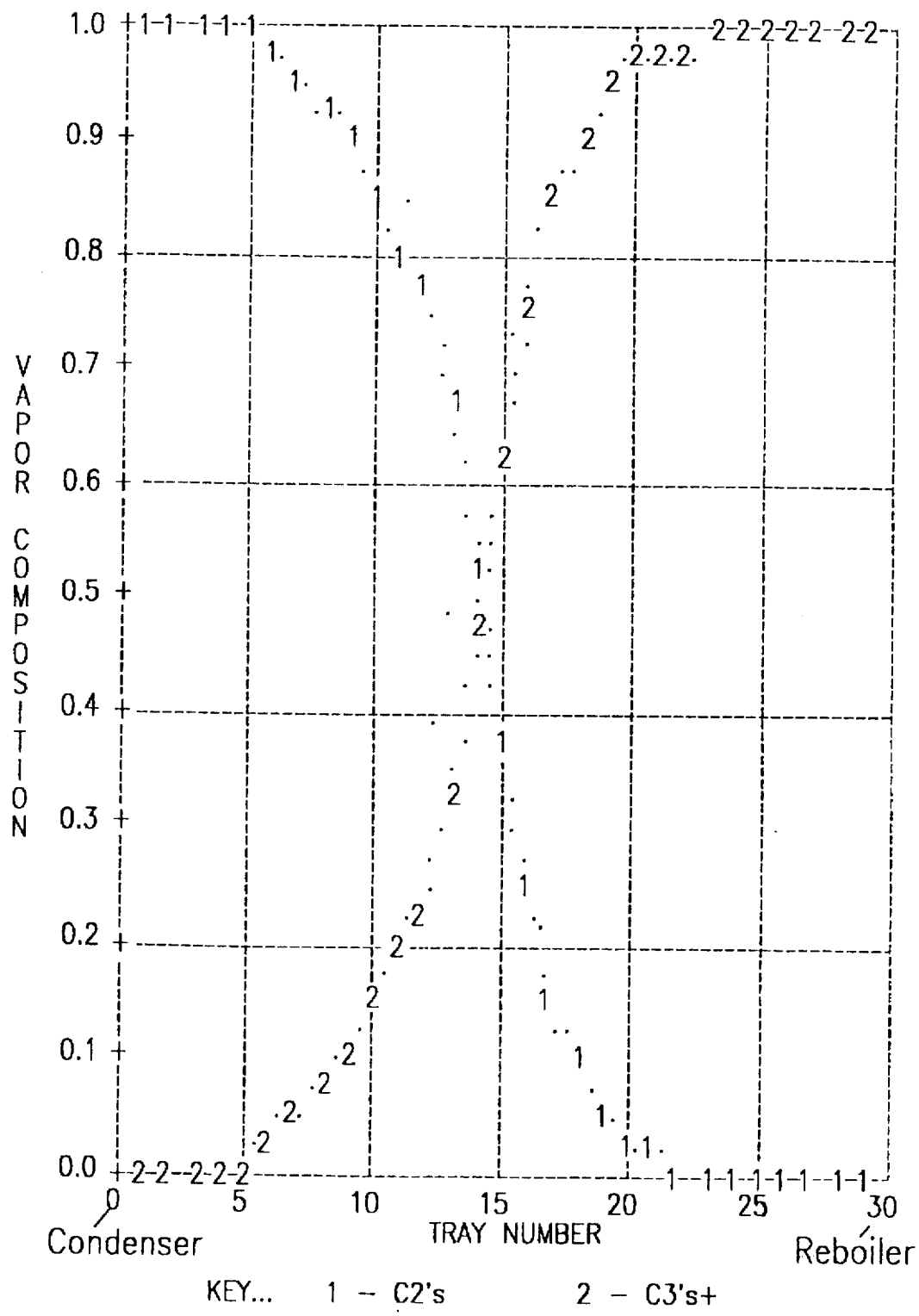
FIG. 4 is a plot of the components ethylene and ethane (Key number 1 on the plot or "C2's") and propylene, propane and butane (Key number 2 of the plot or "C3's+"). The relative vapor compositions of the two keys are plotted against actual tray number for operation of a deethanizer according to the prior art deethanizer described in FIG. 1. A "Condenser" notation indicates the top of the column on the x-axis of the plot. A "Reboiler" notation indicates the bottom of the column on the x-axis of the plot.
Figure 5:
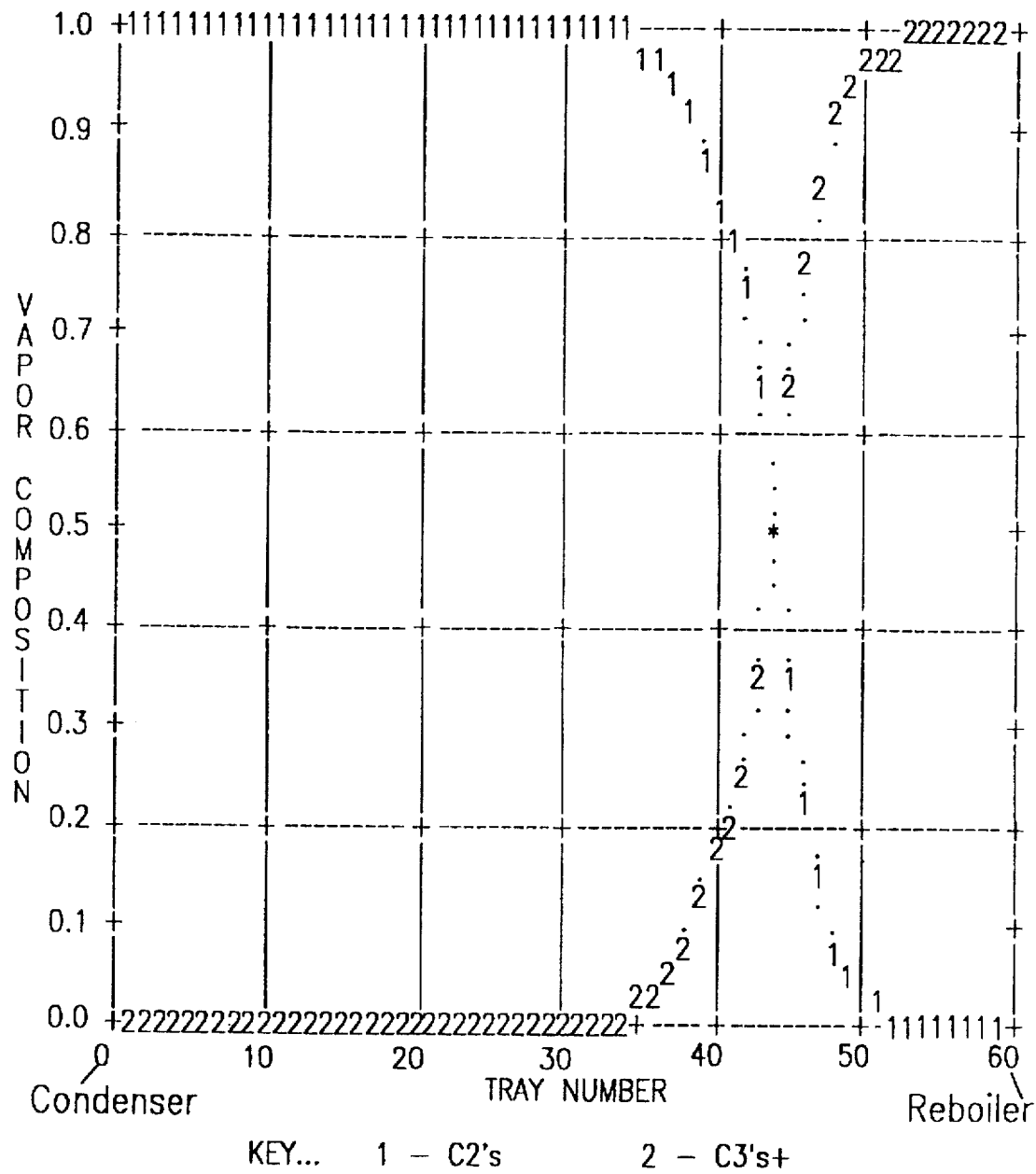
FIG. 5 is a plot of the components ethylene and ethane (Key number 1 on the plot or "C2's") and propylene, propane and butane (Key number 2 of the plot or "C3's+"). The relative vapor compositions of the two keys are plotted against actual tray number for operation of a deethanizer according to the prior art deethanizer described in FIG. 2. A "Condenser" notation indicates the top of the column on the x-axis of the plot. A "Reboiler" notation indicates the bottom of the column on the x-axis of the plot.

In addition, FIGS. 4 and 5 are included to indicate the change in composition of the vapor streams in columns 100 and 200. The pattern of separation of keys 1 and 2 are similar in FIGS. 4 and 5, although it is evident that the same degree of separation takes place with fewer actual trays for the deethanizer of the present invention, whose operation is shown in FIG. 5, when compared to the number of actual trays required for the same separation in the prior art deethanizer, whose operation is shown in FIG. 4.

TABLE 1

| Stream No. | 100 (upr) | 100 (lwr) | 101 | 102 | 104 | 109 | 110 |
|---|---|---|---|---|---|---|---|
| Temp. °F. | −11 | 61 | 108 | −32 | −105 | 90 | −30 |
| Press. psia | 240 | 240 | 242 | 232 | 59 | 102 | 241 |
| Vapor frac | 1.00 | 0.00 | 0.00 | 0.00 | 1.00 | 1.00 | 0.00 |
| Components Lb-mol/hr | | | | | | | |
| Methane | 0.3 | 0.3 | | 0.6 | 1.7 | | 0.6 |
| Ethylene | 3425.9 | 2938.3 | | 6364.2 | 17796.1 | 3.5 | 6360.7 |
| Ethane | 320.6 | 496.9 | 0.3 | 817.2 | 10.9 | 809.4 | 7.8 |
| MAPD | 0.7 | 17.3 | 18.0 | | | | |
| Propylene | 143.7 | 1365.7 | 1503.1 | 6.3 | | 6.3 | |
| Propane | 66.1 | 847.2 | 912.6 | 0.7 | | 0.7 | |
| C4's | 0.1 | 9.4 | 9.5 | | | | |

TABLE 2

| Stream No. | 200 (upr) | 200 (lwr) | 201 | 202 | 203 | 205 | 210 | 211 |
|---|---|---|---|---|---|---|---|---|
| Temp. °F. | −11 | 61 | 112 | −26 | −33 | −105 | 90 | −30 |
| Press. psia | 240 | 240 | 253 | 232 | 240 | 59 | 102 | 241 |
| Vapor frac | 1.00 | 0.00 | 0.00 | 0.00 | 0.00 | 1.00 | 1.00 | 0.00 |
| Components | | | | | | | | |

TABLE 2-continued

| Stream No. | 200 (upr) | 200 (lwr) | 201 | 202 | 203 | 205 | 210 | 211 |
|---|---|---|---|---|---|---|---|---|
| Lb-mol/hr | | | | | | | | |
| Methane | 0.3 | 0.3 | | 0.1 | 0.5 | 0.18 | | 0.1 |
| Ethylene | 3425.9 | 2938.3 | | 4310.0 | 2054.2 | 12077.6 | 3.5 | 2050.7 |
| Ethane | 320.6 | 496.9 | 0.3 | 816.4 | 0.8 | 7.41 | 813.2 | 3.2 |
| MAPD | 0.7 | 17.3 | 18.0 | | | | 3.2 | |
| Propylene | 143.7 | 1365.7 | 1504.8 | 4.6 | | | | |
| Propane | 66.1 | 847.2 | 912.9 | 0.4 | | | | |
| C4's | 0.1 | 9.4 | 9.5 | | | | | |

TABLE 3

| Exch. No. | E100 | E101 | E102 | E103 & E104 | E105 | E107 | E108 |
|---|---|---|---|---|---|---|---|
| Duty, MMBtu/hr | 29.4 | 50.9 | 16.6 | 69.4 | 3.1 | 4.2 | 40.66 |

| Exch. No. | E200 | E201 | E202 | E203 & E204 | E205 | E207 | E208 |
|---|---|---|---|---|---|---|---|
| Duty, MMBtu/hr | 29.6 | 50.7 | 13.7 | 44.4 | 4.0 | 4.2 | 35.4 |

TABLE 4

| Stage No. | S100 | S101 | S102 |
|---|---|---|---|
| HP | 792 | 9657 | BASE |

| Stage No. | S200 | S201 | S202 |
|---|---|---|---|
| HP | 792 | 7307 | BASE-996 |

I claim:

1. A process for separating ethylene and ethane from light hydrocarbons in a deethanizer feed through the use of a deethanizer with a rectification section above a feed stage, a stripping section below the feed stage and an overhead condenser above a top stage of the rectification section providing refluxing duty to the deethanizer, comprising the steps of:
   (a) feeding the deethanizer feed into the feed stage and performing separation of ethylene and ethane from heavier feed components between the feed stage and a sidedraw withdrawal stage, wherein the sidedraw withdrawal stage is located between the feed stage and the top stage of the deethanizer; and
   (b) withdrawing at least 5 percent of the ethane in the feed in a sidedraw stream at the sidedraw withdrawal stage such that no portion of the sidedraw stream is returned to the deethanizer.

2. The process of claim 1 wherein the sidedraw withdrawal stage is located at least 5 stages below the top stage.

3. The process of claim 2 wherein overhead product of the deethanizer is a stream comprising from 90 to 99.9 mole percent ethylene.

4. The process of claim 3 wherein from 7 to about 45 trays are located in the deethanizer between the sidedraw withdrawal stage and the overhead condenser.

5. The process of claim 4 wherein 5 to 99 percent of the ethane in the deethanizer feed is recovered in the sidedraw stream.

6. The process of claim 5 comprising the further step of:
   (c) feeding the sidedraw stream to a low pressure, heat pumped C2 splitter and fractionating the sidedraw stream in the C2 splitter.

7. The process of claim 6 comprising the further step of:
   (d) condensing a vapor stream from the top stage of the deethanizer and a top stage of the C2 splitter in a heat exchanger.

8. The process of claim 1 wherein the deethanizer operates at about 240 psia.

9. A process for separating a first column overhead product from a first column feed in a first column with a rectification section above a feed stage, a stripping section below the feed stage and an overhead condenser above a top stage of the rectification section providing refluxing duty to the first column, wherein the first column overhead product comprises a first product hydrocarbon component with a first boiling temperature and a second product hydrocarbon component with a second boiling temperature which is less that the first boiling temperature, wherein the first column feed is a hydrocarbon feed in which substantially no components of the first column feed have lower boiling temperatures than the first boiling temperature, comprising the steps of:
   (a) feeding the first column feed to the feed stage and separating the first and the second column overhead products from heavier feed components between the feed stage and a sidedraw withdrawal stage in the rectification section, wherein the sidedraw withdrawal stage is located between the feed stage and the top stage of the first column;
   (b) withdrawing at least 5 percent of the first product hydrocarbon component in a sidedraw stream at the sidedraw withdrawal stage such that no portion of the sidedraw stream is returned to the first column;
   (c) obtaining an overhead product stream from the first column with more than about 90 mole percent of the second product hydrocarbon component contained in the first column feed; and
   (d) feeding the sidedraw stream to a second column at a second column feed stage and fractionating the sidedraw stream in the second column to separate the first and the second product hydrocarbon components.

10. The process of claim 9 wherein the first column overhead product stream is fed to the second column at a first column overhead product feed stage nearer the top stage of the second column than the second column feed stage.

11. The process of claim 9 wherein more than 7 trays are located in the first column between the first column condenser and the sidedraw withdrawal stage.

12. The process of claim 9 wherein the amount of the second product hydrocarbon product in the first column feed recovered to the first column overhead product stream is greater than about 20 percent and its purity in the overhead product stream is greater than about 90 mole percent.

* * * * *